(12) United States Patent
Smith (10) Patent No.: US 10,525,245 B2
(45) Date of Patent: Jan. 7, 2020

(54) TATTOO MACHINE CAMERA ASSEMBLY

(71) Applicant: Lindsay Smith, San Francisco, CA (US)

(72) Inventor: Lindsay Smith, San Francisco, CA (US)

( * ) Notice: Subject to any disclaimer, the term of this patent is extended or adjusted under 35 U.S.C. 154(b) by 0 days.

(21) Appl. No.: 15/856,068

(22) Filed: Dec. 28, 2017

(65) Prior Publication Data

US 2018/0177992 A1   Jun. 28, 2018

Related U.S. Application Data

(60) Provisional application No. 62/439,578, filed on Dec. 28, 2016.

(51) Int. Cl.
*H04N 5/225* (2006.01)
*A61M 37/00* (2006.01)
*H04N 5/232* (2006.01)

(52) U.S. Cl.
CPC ...... *A61M 37/0076* (2013.01); *H04N 5/2252* (2013.01); *H04N 5/2254* (2013.01); *H04N 5/2256* (2013.01); *H04N 5/2257* (2013.01); *H04N 5/2328* (2013.01); *A61M 2205/3306* (2013.01)

(58) Field of Classification Search
None
See application file for complete search history.

(56) References Cited

U.S. PATENT DOCUMENTS

| | | | | |
|---|---|---|---|---|
| 2008/0027279 A1* | 1/2008 | Abou El Kheir | .... | A61B 1/0008 600/111 |
| 2010/0328791 A1* | 12/2010 | Jung | ...... | G03B 17/02 359/824 |
| 2016/0022374 A1* | 1/2016 | Haider | ...... | A61B 17/17 606/96 |
| 2016/0030134 A1* | 2/2016 | Shapter | ...... | G06F 3/0488 606/130 |

\* cited by examiner

*Primary Examiner* — Eileen M Adams
(74) *Attorney, Agent, or Firm* — Kevin M. Chrustowski (57) ABSTRACT

A tattoo machine camera assembly comprises a camera assembly coupled to a tattoo machine. The tattoo machine camera assembly further comprises a camera mount for coupling the camera assembly to the tattoo machine. The camera mount may be formed separately from the tattoo machine or formed integrally with the tattoo machine. The tattoo machine camera assembly may be formed so that the camera is resistant to vibration created by the operation of the tattoo machine. A method of video recording the tattooing process may also be implemented.

15 Claims, 7 Drawing Sheets

TATTOO MACHINE CAMERA ASSEMBLY

CROSS REFERENCE TO RELATED APPLICATIONS

This application claims priority to U.S. Provisional Patent Application No. 62/439,578, filed Dec. 28, 2016, entitled "Tattoo Machine Camera Assembly," which is incorporated herein by reference in its entirety.

TECHNICAL FIELD

The present disclosure relates to a tattoo machine camera assembly. In particular, the disclosure relates to a camera assembly coupled to a tattoo machine for recording the tattooing process.

BACKGROUND

Tattoos are a popular form of art used for personal expression. Tattoo machines are used to apply tattoos to the skin, puncturing the skin and depositing ink under the top layer of skin. Some locations where tattoos may be applied are difficult, or even impossible, for the recipient to observe during the tattooing process. This can make the experience less enjoyable and make it difficult for the recipient to approve changes during the process. Some tattoo artists use tripods with attached cameras in order to record the tattooing process, however this has many disadvantages. These disadvantages include, but are not limited to, the distance between the camera and the tattoo, the stationary nature of the tripod, and the space required for the tripod which can interfere with the artist. Other tattoo artists use cameras attached to their bodies. These suffer similar problems as tripod cameras in addition to having a non-ideal point of view. Also, many tattoo artists do not record the tattooing process at all. Therefore, there is a need for a tattoo machine camera assembly capable of video recording the tattooing process that enhances the experience for both the artist and the recipient.

SUMMARY

An embodiment includes a tattoo machine camera assembly comprising a tattoo machine and a camera assembly coupled to the tattoo machine. The tattoo machine may include a frame and a grip. The camera assembly may be coupled to the tattoo machine by way of a camera mount. The camera mount may be coupled to the frame or the grip. The camera assembly may be coupled to the camera mount, enabling an enhanced recording of the tattooing process that is not possible with today's conventional camera systems.

By recording the tattooing process from the point of view of a tattoo needle, the recipient can get a close, ideal view of the tattoo, regardless of where the tattoo is being applied. This will drastically improve the collaboration between the artist and the recipient. The comfort level of the recipient would also be drastically improved during the tattooing process, which can sometimes last as long as 8 hours or more. In another embodiment, a method of recording the tattooing process is provided. The method comprises the steps of providing a tattoo machine with a camera assembly coupled to the tattoo machine, applying a tattoo, and recording the tattooing process with the camera. It is also contemplated that the video may be streamed live over the internet to a website or mobile app for mobile devices, such as smartphones and tablets. This would allow the tattoo recipient to view a live stream of the tattooing process in order to make comments and review the artist's work as it happens without having to strain or contort their body or neck to view the process. It is also contemplated that the video may be sent over a local wired or wireless network to a device that can be viewed by the tattoo recipient without requiring an internet connection. In addition to live streaming, the process may be recorded and kept for personal use, such as sharing on social networks at a later time, for example.

DETAILED DESCRIPTION

The following detailed description is not intended to include every embodiment that is currently contemplated by the inventor. It is to be understood that embodiments not explicitly described herein would be known by a person of ordinary skill in the art to be within the scope of the description that follows and the appended claims.

As shown in the accompanying figures, a coil tattoo machine is used for the following description. It should be understood that those skilled in the art would understand that a rotary tattoo machine could also be used. Though the coil and rotary tattoo machines are most common and very well known in the art, it should be understood that any type of tattoo machine could be used for the tattoo machine camera assembly as disclosed herein.

Referring to FIG. 1-8, a tattoo machine camera assembly 1 is shown. Tattoo machine camera assembly 1 includes a frame 2 and a grip 13. A camera assembly 11 is coupled to the frame 2 via a camera mount 3. The camera assembly 11 includes a camera housing 5, a camera 6, a light source 12, an adjustable arm 4, and a power/data cable 9. The camera housing 5 may be a copper housing, for example, that provides electrical shielding and physical protection for the camera. Any material capable of providing electrical shielding and protection is contemplated for camera housing 5. Camera 6 is coupled to a distal end of camera housing 5, such as by crimping the housing 5 about the camera 6, for example. The adjustable arm 4 is capable of being positioned in a multitude of different positions desirable by the tattoo artist or tattoo recipient, giving the camera 6 a viewpoint which includes the tattoo machine grip 13 and needle 14. This provides a close-up view of the tattoo during the tattooing process. In alternative embodiments, the camera assembly 11 may be coupled to the camera mount 3 without using an adjustable arm 4, wherein the camera housing 5 may be directly coupled to the camera mount 3.

The camera assembly 11 may alternatively comprise a stationary, rigid arm and be coupled to the camera mount 3 in a fixed position.

Figure 6:
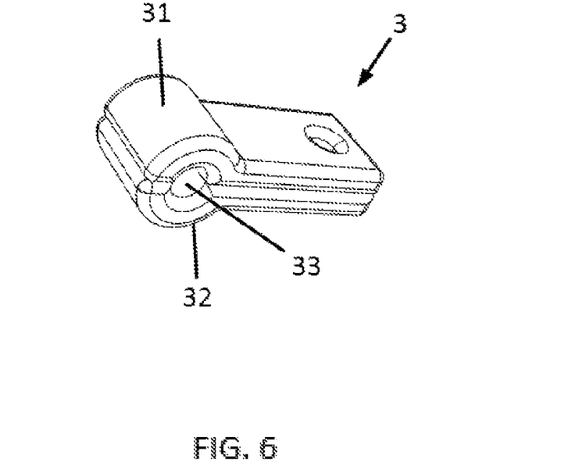
FIG. 6 is a perspective view of the camera mount of FIG. 4.
Figure 7:
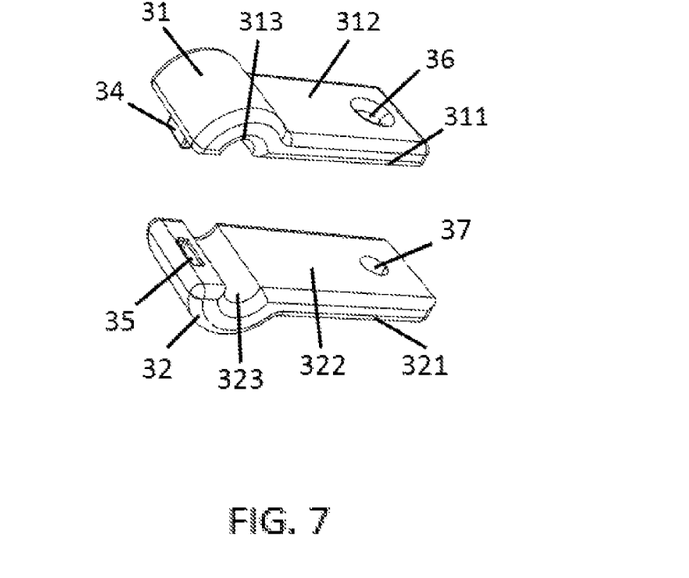
FIG. 7 is an exploded view of the camera mount of FIG. 6.
Figure 8:
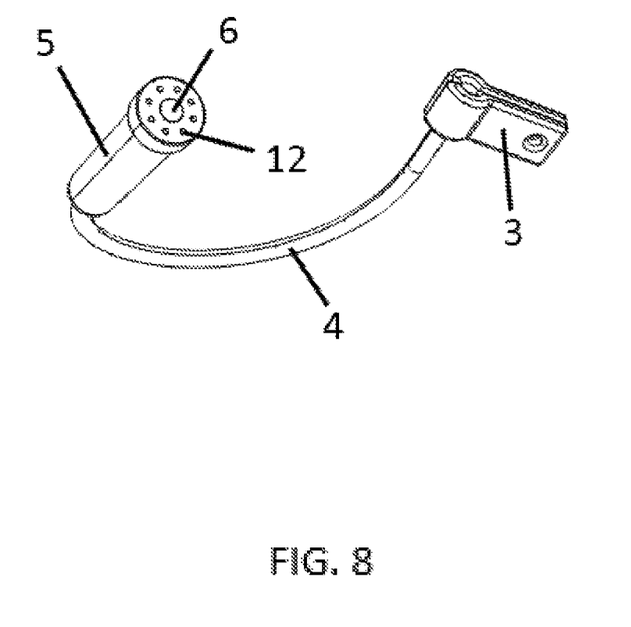
FIG. 8 is a perspective view of the camera assembly of FIG. 5 coupled to the camera mount of FIG. 6.

As shown in FIG. 6-7, a camera mount 3 in shown disassembled from the tattoo machine frame 2. Camera mount 3 comprises a first mount portion 31 and a second mount portion 32. First mount portion 31 comprises a first mount portion first surface 311 and a first mount portion second surface 312. Second mount portion 32 comprises a second mount portion first surface 321 and a second mount portion second surface 322. First mount portion 31 further comprises a protrusion 34 which axially aligns with a groove 35 formed in the second mount portion 32. When the camera mount 3 is assembled and coupled to the frame 2, first mount portion first surface 311 abuts second mount portion second surface 322 and protrusion 34 forms an interference press fit in groove 35. Orifice 36 in the first mount portion 31 axially aligns with orifice 37 in the second mount portion 32 and fastener 7 is passed through both orifices and thereby couples the camera mount 3 to the frame 2, as seen in FIG. 4 for example.

Figure 1:
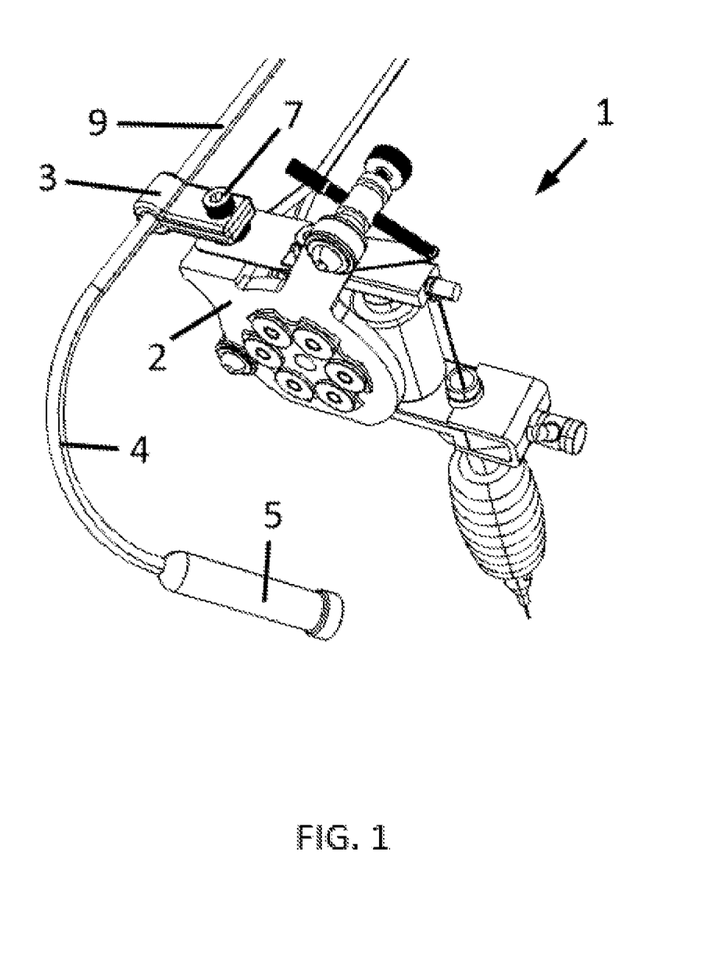
FIG. 1 is a top perspective view of a tattoo machine camera assembly according to one embodiment.
Figure 2:
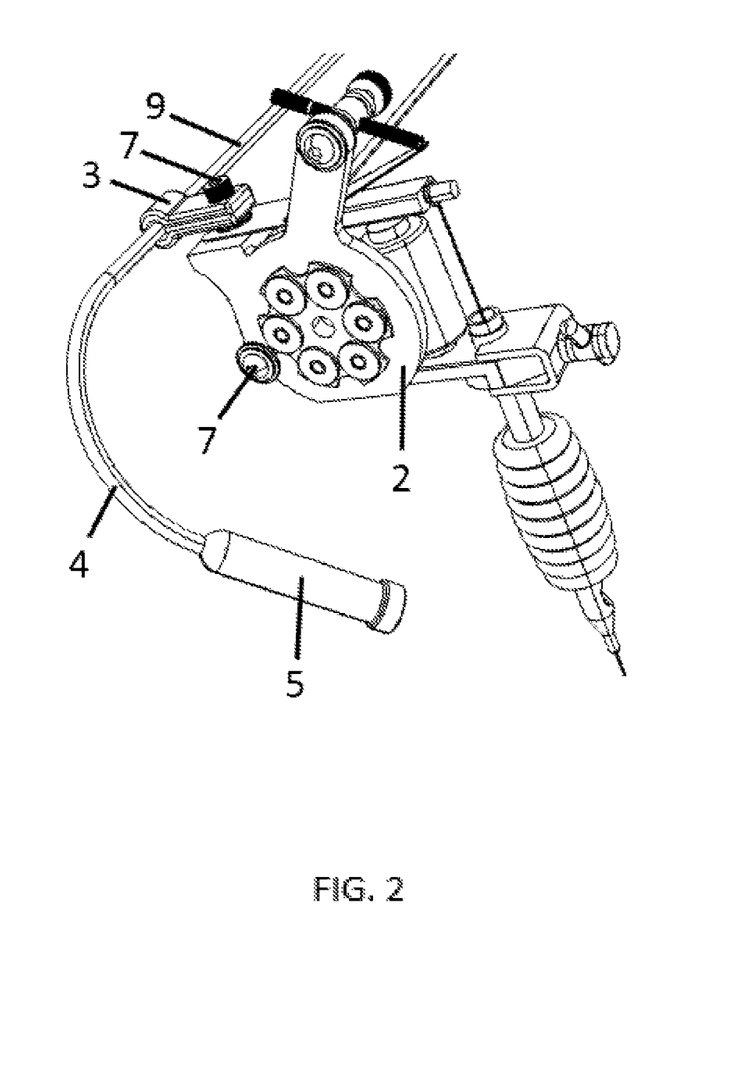
FIG. 2 is a side perspective view of the tattoo machine camera assembly of FIG. 1.
Figure 3:
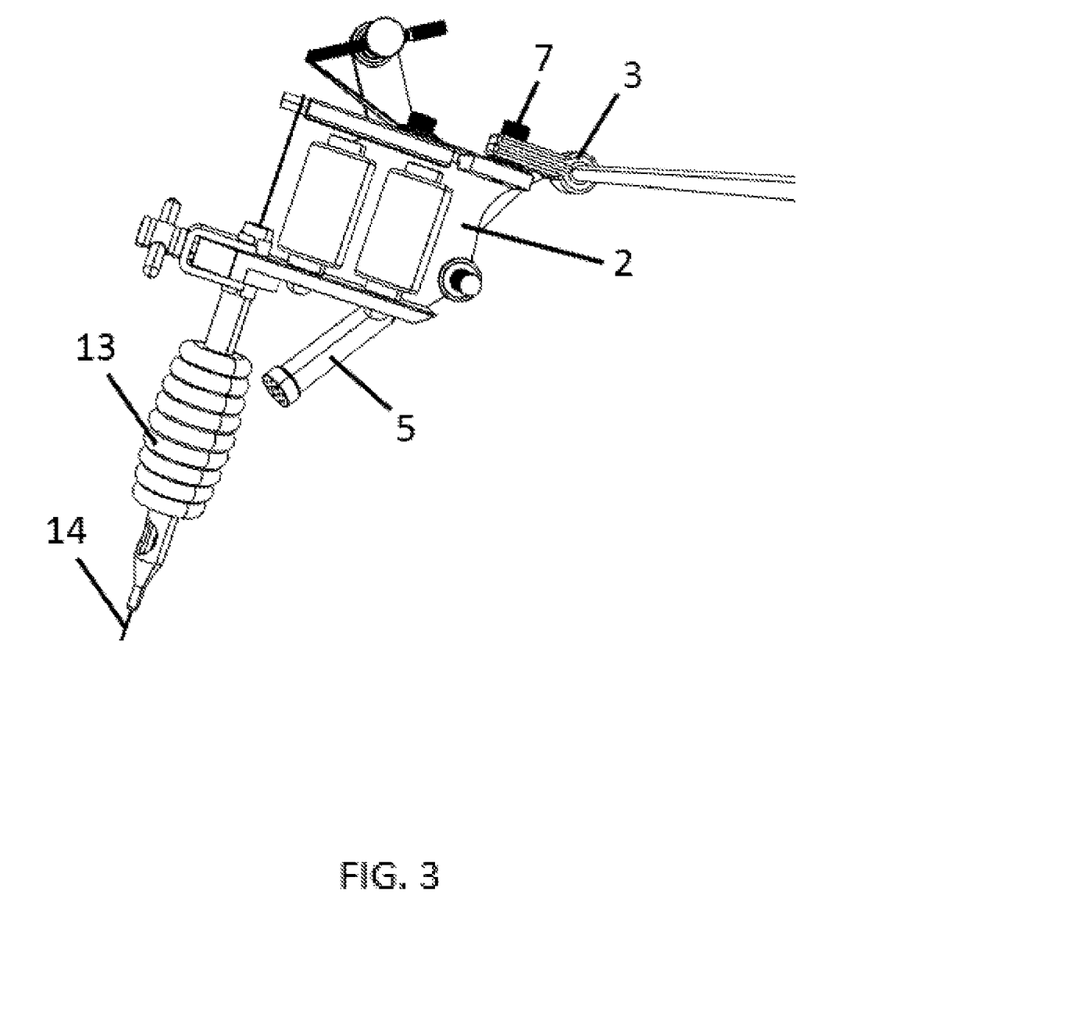
FIG. 3 is a side perspective view of the tattoo machine camera assembly of FIG. 1.
Figure 4:
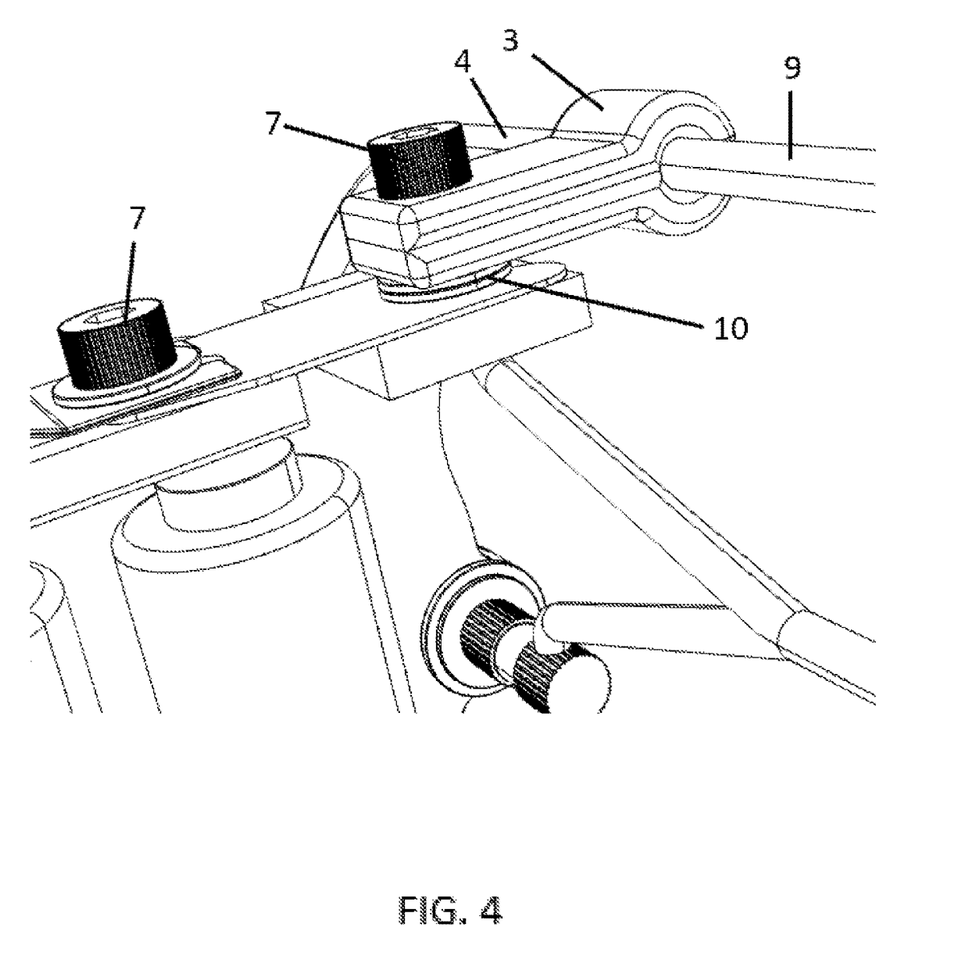
FIG. 4 is a perspective view of a camera mount according to one embodiment.
Figure 5:
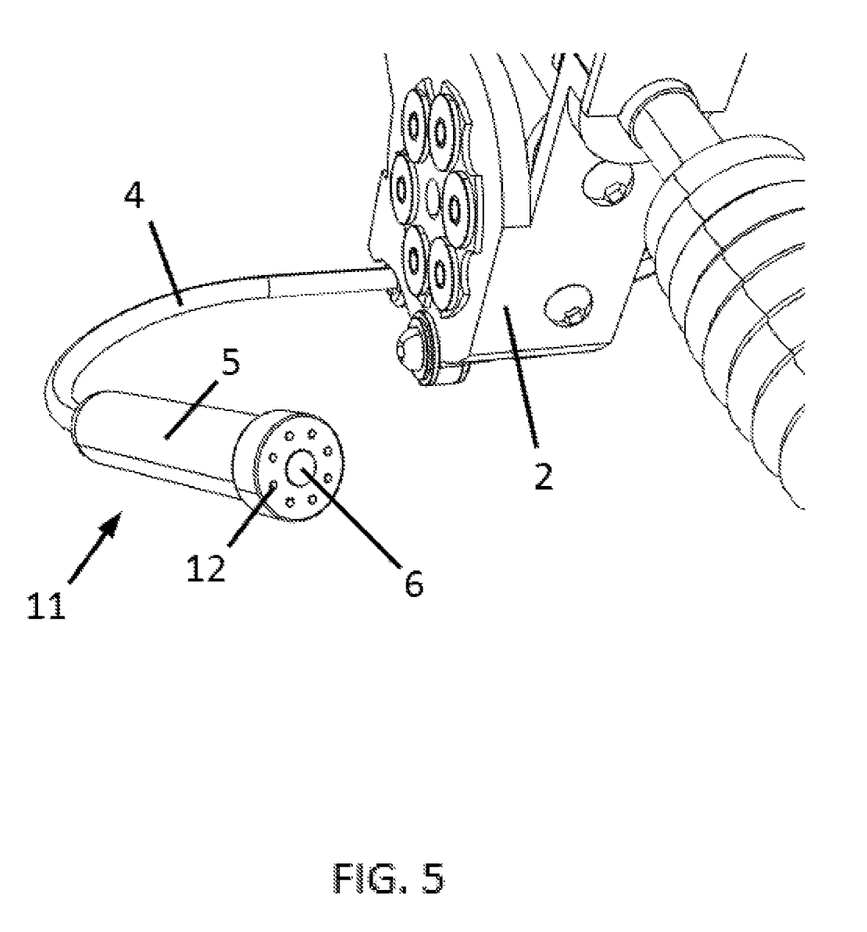
FIG. 5 is a perspective view of a camera assembly according to one embodiment.

As further shown in FIG. 4, a washer 10 may be placed between the frame 2 and the second mount portion first surface 321. Washer 10 may be a standard metal washer as known in the art, but preferably washer 10 is made from a vibration dampening material, such as a semi-rigid or elastic material, for example a plastic or rubber material. When rubber or other elastic materials are used, vibration from the operation of the tattoo machine may be at least partially absorbed and therefore the effects on the camera footage may be minimized. In this way, a smoother video may be captured and thus maximize the effectiveness of filming the tattooing process. Alternatively, or in addition, an elastic material may be placed between the washer 10 and the second mount portion first surface 321 to similarly minimize vibration of the camera assembly 11.

The camera mount 3 may be made of metal or a metal alloy, such as aluminum or steel for example. Camera mount 3 may also be formed from alternative materials such as plastic. Mount coupling gap 33 is formed between the first 31 and second 32 mount portions, allowing mounting of the adjustable arm 4, or camera housing 5, to the camera mount 3. According to the one embodiment, the mount coupling gap 33 may be formed in the space between first mount portion arcuate surface 313 and second mount portion arcuate surface 323. Depending on the diameter of the adjustable arm 4, or camera housing 5, the mount coupling gap 33 may be formed larger or smaller by adjusting the dimensions of the first 313 and second 323 mount portion arcuate surfaces during fabrication. As is seen in FIG. 1-5, the camera assembly 11 is coupled to the frame 2 via the camera mount 3 by placing the adjustable arm 4 along the second mount portion arcuate surface 323 and assembling and coupling the camera mount 3 to the frame 2 as previously described. Alternatively, the camera housing 5 may be coupled to the frame 2 via the camera mount 3 by placing the camera housing 5 along the second mount portion arcuate surface 323 and assembling and coupling the camera mount 3 to the frame 2 as previously described. It should be understood that alternative embodiments of the camera housing 5 may be used, such that camera 6 and any related camera components may be directed coupled to the camera mount 3.

In one embodiment, camera mount 3 comprises orifices 36 and 37 which allow coupling of the camera mount 3 to the frame 2 via fastener 7. Frame 2 has several fasteners 7 holding together the components of the tattoo machine. For simplicity, all the figures show the same attachment point, however any fastener location may be used for attaching the camera mount 3. Each location could provide different viewing angles and optimum performance of the system depending on the desires of the artist and recipient. For example, the tattoo artist may be left or right-hand dominant, and thus the artist could arrange the camera mount on the appropriate fastener location to avoid any interference. As shown, fasteners 7 are of nut and bolt type configurations, allowing the bolt to pass through the orifices 36 and 37 thereby coupling the camera mount 3 to the frame 2. It should be understood that the camera mount 3 may be coupled to the frame 2 via other methods, such as an adhesive, without departing from the scope of this disclosure. The camera mount 3 could also be at least partially integrally formed with the frame 2 by such processes as metal casting or plastic injection molding. For example, the second mount portion 32 may be formed integrally with the frame 2 and the first mount portion 31 may be formed separately and coupled to the second mount portion 32 as previously described.

Adjustable arm 4 may be made from a flexible plastic with a hollow interior, serving to protect and house the camera power/data cable 9. Camera housing 5 is crimped about a first end of the adjustable arm 4. A second end opposite the first end of the adjustable arm 4 is coupled to the camera mount 3 as previously described. The adjustable, flexible nature of the adjustable arm 4 allows for positioning the camera 6 in a multitude of different positions for optimum viewing of the tattooing process. The tattoo artist may also use the adjustable arm 4 to place the camera 6 in a position that does not interfere with the application of the tattoo. Other materials may be used for the adjustable arm 4, such as rubber or metal, provided it maintains its adjustable nature while also remaining semi-rigid so that the adjustable arm 4 can remain relatively stationary once positioned by the artist. The combination of the semi-rigid yet flexible adjustable arm 4 with a vibration dampening material, such as washer 10 as previously described, helps to ensure minimal vibration of the camera 6 resulting from operation of the tattoo machine.

Adjustable arm 4 may also be formed from alternative materials and be in alternative forms. Adjustable arm 4 may be constructed from a flexible, coated wire coil or be a jointed ball and socket linkage. Other alternatives include rigid members connected by locking mechanisms, allowing movement about a point location, such as an elbow. The camera assembly 11 may include a swivel feature, giving even more freedom of motion to the camera 6 to ensure optimum video recording.

The tattoo machine camera assembly 1 may also include other anti-vibration features. By selectively choosing the material of construction of the adjustable arm 4 and tuning its flexibility, for example by changing the wall thickness, vibration of the camera 6 can be minimized. Alternatively, a vibration dampening material may be placed within the adjustable arm 4. If the camera housing 5 is directly mounted to the camera mount 3 without using adjustable arm 4, a vibration dampening material may be positioned between the camera mount 3 and the camera housing 5. The camera assembly 11 may include the vibration dampening material within the camera 6 or camera housing 5. Vibration dampening materials may include rubber or springs, for example. By limiting the effects of vibration from the tattoo machine operation and tattoo artist movement, the video feed will have optimum clarity.

The camera 6 can be any camera capable of recording video. It may also be capable of taking still images, i.e. photographs. The camera may be lightweight and of a small packaging size, such as those found in popular smartphones and tablets. It should be well understood by those skilled in the art of tattooing that minimum weight and size is optimum for coupling the camera 6 to the tattoo machine frame 2 and maintaining ease of operation. Camera power/data cable 9 may be coupled to the camera 6 and extend through the camera housing 5 and the adjustable arm 4. Camera power/data cable 9 may end in a universal serial bus (USB) interface, for example, for attaching to a computer or power source for electrical power and video data transmission. Other connections for electrical power and data transmission may be used and should not be considered to limit the scope of this disclosure. More than one camera power/data cable 9 may be used, such as one for electrical power and one for data transmission. In an alternative embodiment, the camera may be wireless and transmit video through a wireless connection to a computer, for example.

Light source 12 may be a single LED or an array of LEDs that surround the camera 6. The tattoo artist can increase or decrease the light intensity from the light source 12 in order to optimize the quality of the video. The recipient may also control the light source 12 to obtain the best view of the tattooing process. Light source 12 may be another type of light emitting device, other than LEDs, and may be mounted anywhere on the tattoo machine camera assembly 1 to provide illumination for the tattooing process. In some embodiments, no light source is required.

It should be understood that the preceding is merely a description of several embodiments and other alternative embodiments. It is not meant to be limiting nor descriptive of every possible embodiment. Persons having ordinary skill in the art will understand that various other embodiments are possible without departing from the scope of the present disclosure and the appended claims.

What is claimed is:

1. A tattoo machine camera assembly comprising,
   a tattoo machine frame;
   a camera mount coupled to the tattoo machine frame;
   a camera assembly coupled to the camera mount;
   wherein the camera assembly comprises a camera and a hollow adjustable arm for housing a camera data/power cable; and
   wherein the hollow adjustable arm comprises a first end and a second end, wherein the camera is coupled to the first end and the camera mount is coupled to the second end.

2. The tattoo machine camera assembly of claim 1, wherein the camera captures video of the tattooing process.

3. The tattoo machine camera assembly of claim 2, wherein the camera captures photographs of the tattooing process.

4. The tattoo machine camera assembly of claim 1, further comprising a vibration dampening material positioned between the frame and the camera mount.

5. The tattoo machine camera assembly of claim 4, wherein the vibration dampening material comprises an elastic material.

6. The tattoo machine camera assembly of claim 1, wherein the camera assembly further comprises a light source.

7. The tattoo machine camera assembly of claim 6, wherein the light source comprises a single light source.

8. The tattoo machine camera assembly of claim 6, wherein the light source comprises a plurality of light sources.

9. The tattoo machine camera assembly of claim 6, wherein the light source comprises an LED.

10. The tattoo machine camera assembly of claim 6, wherein the camera assembly further comprises a camera housing.

11. A tattoo machine camera assembly comprising,
    a tattoo machine frame;
    a camera mount coupled to the tattoo machine frame;
    and a camera assembly coupled to the camera mount;
    wherein the camera mount comprises a first mount portion and a second mount portion;
    wherein the first mount portion comprises a protrusion and the second mount portion comprises a groove, and wherein the protrusion forms an interference press fit with the groove thereby coupling the camera assembly between the first mount portion and the second mount portion;
    wherein the camera assembly comprises a camera and a hollow adjustable am for housing a camera data/power cable;
    wherein the hollow adjustable arm comprises a first end and a second end; and
    where in the camera is coupled to the first end and the second end is coupled between the first mount portion and the second mount portion.

12. The tattoo machine camera assembly of claim 11, further comprising a vibration dampening material positioned between the second mount portion and the frame.

13. The tattoo machine camera assembly of claim 12, wherein the vibration dampening material comprises an elastic material.

14. A tattoo machine camera assembly comprising,
    a tattoo machine frame;
    a camera assembly coupled to the tattoo machine frame;
    a camera mount, wherein the camera assembly is coupled to the camera mount, and
    wherein the camera mount is coupled to the frame;
    wherein the camera mount comprises a first mount portion and a second mount portion defining a mount coupling gap therebetween;
    wherein the camera assembly comprises a hollow adjustable arm and a camera, wherein the hollow adjustable arm comprises a first end coupled to the camera and a second end coupled in the mount coupling gap.

15. The tattoo machine camera assembly of claim 14, wherein the second mount portion is integrally formed with the frame.

* * * * *